US007418962B1

(12) United States Patent
Rao

(10) Patent No.: US 7,418,962 B1
(45) Date of Patent: Sep. 2, 2008

(54) INHALER FOR AEROSOL MEDICATION

(76) Inventor: C. P. Rao, 19 W. Main St., Mohawk, NY (US) 13407

( * ) Notice: Subject to any disclaimer, the term of this patent is extended or adjusted under 35 U.S.C. 154(b) by 0 days.

(21) Appl. No.: 11/892,511

(22) Filed: Aug. 23, 2007

Related U.S. Application Data

(60) Provisional application No. 60/924,681, filed on May 25, 2007.

(51) Int. Cl.
*A61M 16/10* (2006.01)

(52) U.S. Cl. ........................... 128/200.24; 128/200.14; 128/203.28

(58) Field of Classification Search ............ 128/205.13, 128/203.12, 203.28, 203.29, 205.11, 205.24, 128/204.29, 200.14, 200.16, 200.23, 200.22, 128/200.24
See application file for complete search history.

(56) References Cited

U.S. PATENT DOCUMENTS

| | | | | |
|---|---|---|---|---|
| 3,994,421 | A | 11/1976 | Hansen | |
| 4,637,528 | A | 1/1987 | Wachinski et al. | |
| 4,641,644 | A | 2/1987 | Andersson et al. | |
| 5,020,530 | A * | 6/1991 | Miller | 128/203.28 |
| 5,505,194 | A | 4/1996 | Adjei et al. | |
| 5,613,489 | A * | 3/1997 | Miller et al. | 128/203.28 |
| 5,809,996 | A | 9/1998 | Alldredge | |
| 5,988,160 | A | 11/1999 | Foley et al. | |
| 6,085,742 | A | 7/2000 | Wachter et al. | |
| 6,206,003 | B1 | 3/2001 | Burch | |
| 6,240,917 | B1 | 6/2001 | Andrade | |
| 6,363,932 | B1 | 4/2002 | Forchione et al. | |
| 6,578,571 | B1 * | 6/2003 | Watt | 128/200.14 |
| 6,595,206 | B2 | 7/2003 | Vito | |
| D480,806 | S | 10/2003 | Engelbreth et al. | |
| 6,679,252 | B2 | 1/2004 | Sladek | |
| 6,748,949 | B2 | 6/2004 | Smaldone | |
| 6,904,908 | B2 | 6/2005 | Bruce et al. | |
| 6,953,039 | B2 | 10/2005 | Scarrott et al. | |

(Continued)

FOREIGN PATENT DOCUMENTS

| | | |
|---|---|---|
| DE | 19700838 | 7/1998 |

(Continued)

OTHER PUBLICATIONS

Rau, Joseph L. et al., "Performance Comparison of Nebulizer Designs: Constant-Output, Breath-Enhanced, and Dosimetric," *Respiratory Care*, vol. 49 No. 2 (Feb. 2004), pp. 174-179.

(Continued)

*Primary Examiner*—Steven O Douglas
(74) *Attorney, Agent, or Firm*—Richard C. Litman

(57) ABSTRACT

The inhaler for aerosol medication is an inhaler having a recirculation chamber or rebreather. The inhaler has an aerosol holding chamber having an inlet end for attaching a holder for aerosol medication or nebulizer device thereto and an outlet end for attachment to a mouthpiece or mask for dispensing the medication or substance to the user, with a recirculation chamber depending from the outlet end of the holding chamber or from a mask extending from the outlet end of the chamber. The recirculation chamber has a filter to capture particles of the dispensed substance and prevent their escape from the device to the ambient air. The recirculation chamber may be folded or collapsed for storage within the volume of the aerosol holding chamber. The aerosol holding chamber may be stored within the recirculation chamber.

20 Claims, 14 Drawing Sheets

U.S. PATENT DOCUMENTS

| | | | | |
|---|---|---|---|---|
| 7,004,162 | B1 | 2/2006 | Foley et al. | |
| 7,013,896 | B2 | 3/2006 | Schmidt | |
| 7,082,947 | B2 | 8/2006 | Smaldone | |
| 2002/0104531 | A1 * | 8/2002 | Malone | 128/200.23 |
| 2003/0168062 | A1 | 9/2003 | Blythe et al. | |
| 2005/0145247 | A1 | 7/2005 | Nashed | |
| 2005/0217667 | A1 | 10/2005 | Dhuper et al. | |
| 2006/0054168 | A1 | 3/2006 | Yu | |
| 2006/0254579 | A1 | 11/2006 | Grychowski et al. | |

FOREIGN PATENT DOCUMENTS

| | | |
|---|---|---|
| EP | 601708 | 6/1994 |
| WO | WO 03/092777 | 11/2003 |

OTHER PUBLICATIONS

Website, http://www.lifeoutcomes.com/id11.html, advertisement for Circulaire® Nebulizer, two sheets printed from the internet on Dec. 27, 2006.

Circulaire® inhaler brochure from Westmed, Inc., dated Jul. 17, 2006, two sheets.

Website, http://www.trudellmed.com/, Aerochamber and Aeroeclipse inhalers and nebulizers from Trudell Medical International, three sheets printed Jan. 28, 2007.

Website,http://www.emedoutlet.com/generic.php?genericid=93 &utm_source=bizrate&utm_campaign=preeti &utm_term=Flovent125mg1OralInhaler, Flovent 125MCG Inhaler, one sheet printed from the internet Mar. 3, 2007.

* cited by examiner

INHALER FOR AEROSOL MEDICATION

CROSS-REFERENCE TO RELATED APPLICATION

This application claims the benefit of U.S. Provisional Patent Application Ser. No. 60/924,681, filed May 25, 2007.

BACKGROUND OF THE INVENTION

1. Field of the Invention

The present invention relates generally to devices for dispensing medication and related substances. More particularly, the present invention relates to an inhaler for aerosol medication.

2. Description of the Related Art

Inhalers for dispensing aerosol medication and related substances have been known for quite some time. These devices are commonly used to dispense medication in aerosol form for asthma attacks and other respiratory and medical conditions. Such devices include metered dose inhalers (MDI) and nebulizers. The MDI includes a canister and a sleeve. The canister releases a measured dose of medication when squeezed that is released as a puff of medication through the sleeve. Nebulizers generally are machines that use an air compressor or the like to convert liquid medication into a fine mist. Nebulizers generally require the use of a power supply, although lightweight, handheld nebulizers that operate on battery power are available. Nebulizers often use a face mask for delivery of the medication.

A problem with such devices is that they are not particularly efficient. Generally, a person suffering from an asthma attack is incapable of taking a deep breath, so much of the medication does not reach the lungs where it is needed, at least in the first few breaths. Consequently, the unabsorbed medication is retained in the mouth and the throat, or may merely be exhaled into the ambient air. For this reason, metered dose inhalers are often used with a spacer (a tube or other reservoir) disposed between the sleeve and the patient's mouth to hold the metered dose of medication until the patient is able to breathe deeply enough to inhale more of the medication into the lungs. Nevertheless, a substantial quantity of the medication does not reach the lungs, and may be exhaled, either mediately after a retention period in the mouth and throat, or immediately.

Such medications (e.g., corticosteroids, long term or short term beta-agonists (bronchodilators), and other medications used in aerosol form to treat certain medical conditions) can be harmful to the eyes. Yet with such relatively simple inhalers, the user, caregivers, and others in the immediate vicinity of the patient are subjected to the aerosolized medication, at least upon exhalation.

German Patent No. 19,700,838, published on Jul. 16, 1998, describes (according to the drawings and English abstract) a tube that connects to an aerosol inhaler, together with a collapsible, flexible bag or pouch extending from the opposite end of the tube. The bag or pouch includes a mouthpiece at the end distal from the tube, with the interior volume of the pouch communicating with that of the tube to allow the nebulized or vaporized substance to flow from the inhaler through the tube and pouch and into the mouth of the user. The pouch is formed of a flexible material and may be collapsed and stored within the tube for compact storage.

Thus, an inhaler for aerosol medication solving the aforementioned problems is desired.

SUMMARY OF THE INVENTION

The inhaler for aerosol medication is an inhaler that includes a recirculation chamber or rebreather. The inhaler includes an aerosol holding chamber having an inlet end for the attachment of a holder of aerosol medication or nebulizer device thereto. The opposite outlet end of the holding chamber attaches to a mouthpiece or mask for dispensing the medication or substance to the user.

The inhaler includes a recirculation chamber depending from the outlet end of the aerosol holding chamber, or from a mask extending from the outlet end of the aerosol holding chamber. The recirculation chamber has a filter at its distal end to capture particles of the dispensed medication or other substance and prevent their escape from the device to the ambient air.

Different valve arrangements may be incorporated in different embodiments of the inhaler to allow or prevent recirculation into and from the aerosol holding chamber and to provide different pathways for the flow. In at least one embodiment, the recirculation chamber may be folded or collapsed for storage within the volume of the aerosol holding chamber. In at least one other embodiment, the aerosol holding chamber may be stored within the recirculation chamber for compact storage.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
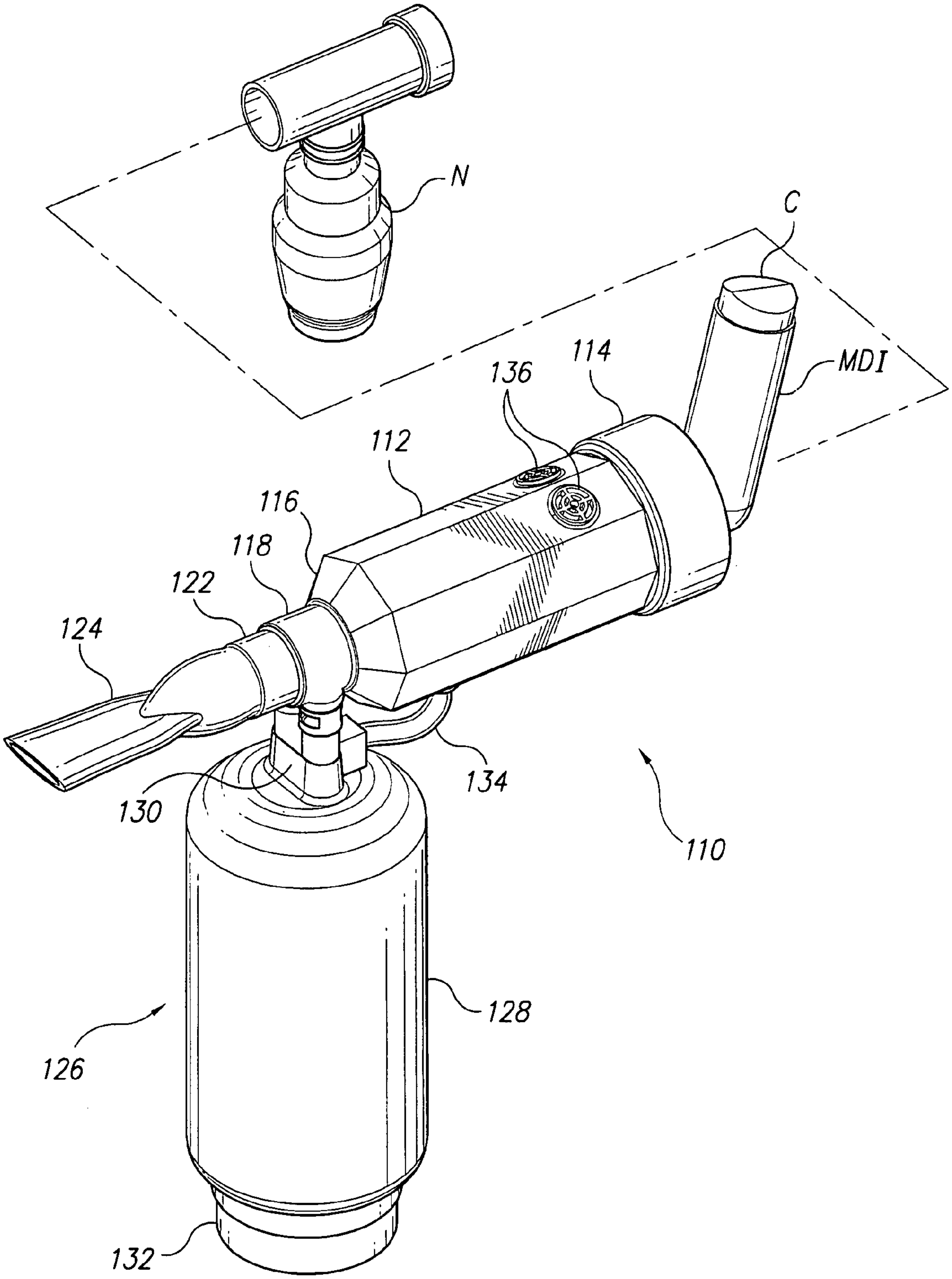
FIG. 1 is a perspective view of a first embodiment of an inhaler for aerosol medication according to the present invention.
Figure 2:
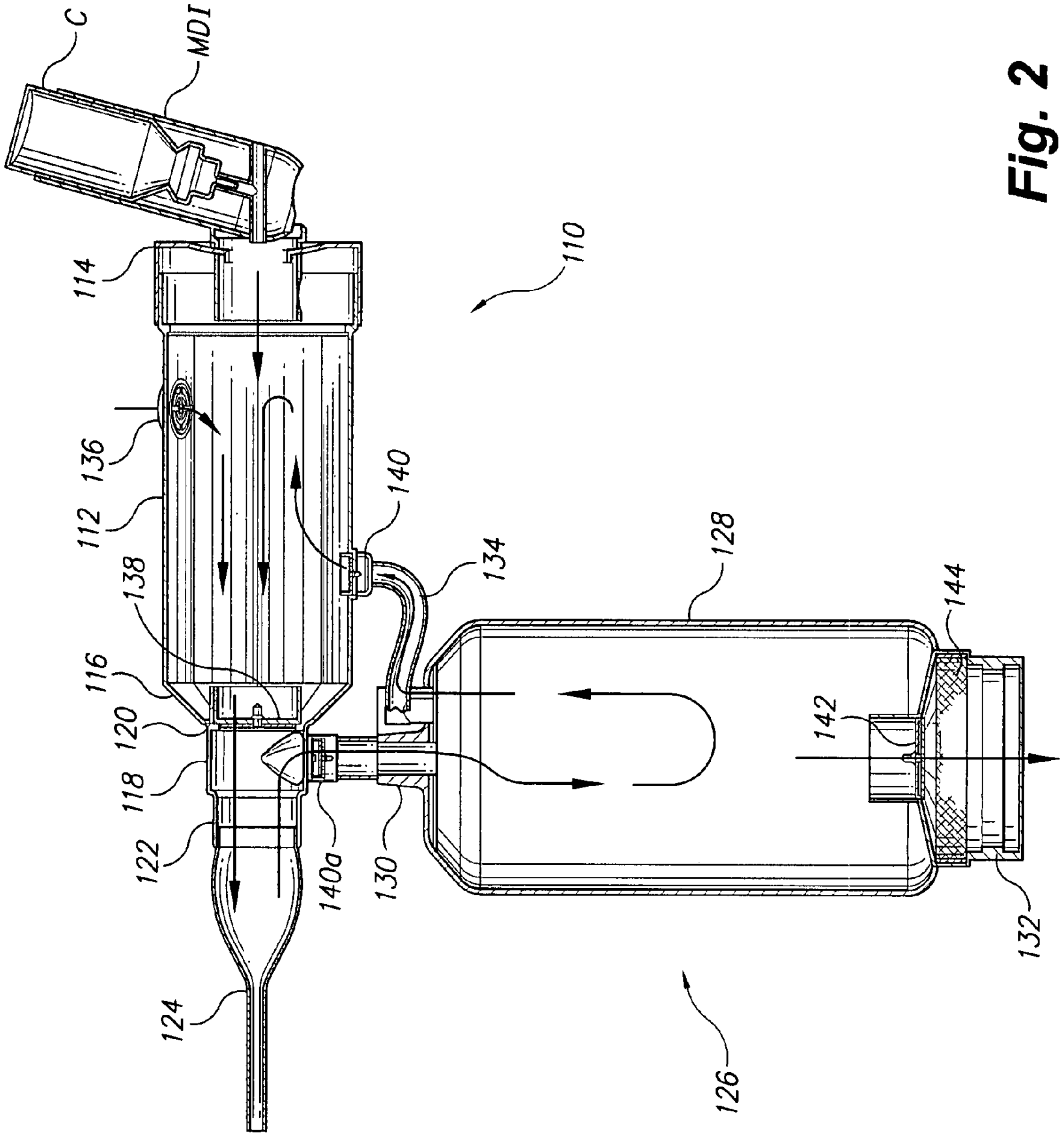
FIG. 2 is a right side elevation view in section of the inhaler of FIG. 1, showing various internal details thereof and the flow path therethrough.

The present invention is an inhaler for aerosol medication having a recirculation chamber with a filtered outlet to preclude or greatly diminish the escape of medication to the ambient air. FIGS. 1 and 2, respectively, provide a perspective view and a right side elevation view in section of a first embodiment of the inhaler 110, in which the inhaler 110 has a rigid recirculation chamber immovably affixed thereto. The inhaler 110 includes a hollow aerosol holding chamber 112 having a medication dispenser attachment end 114 and a delivery end 116 opposite the dispenser attachment end 114. The dispenser attachment end 114 may accept a conventional metered dose inhaler (MDI) with its manually operated medication container or canister C, or, alternatively, a nebulizer N may be attached to the medication dispenser attachment end 114 of the aerosol holding chamber 112, as shown in FIG. 1. The aerosol holding chamber 112 may have an octagonal cross section, as shown, or may have any other regular or irregular geometric cross-sectional shape, as desired.

An intermediate tube 118 extends from the delivery end 116 of the chamber 112, with the intermediate tube having a first end 120 attached to the delivery end 116 of the chamber 112 and an opposite user interface device attachment end 122 extending therefrom. A user interface device, e.g., a mouthpiece 124, as shown in FIGS. 1 and 2, may be removably or permanently affixed to the user interface device attachment end 122 of the intermediate tube 118.

A recirculation chamber 126 has a rigid shell 128 with an attachment end 130 connected to, and communicating with, the intermediate tube 118, and an opposite, distal end 132. The recirculation chamber 126 may have any practicable geometric cross-sectional shape or configuration, as desired. An additional recirculation feedback passage 134 extends from the attachment end 130 of the recirculation chamber 126 to the aerosol holding chamber 112, with the recirculation passage 134 communicating with the intermediate tube 118 of the embodiment 110 of FIGS. 1 and 2 by means of the connection of both the delivery end 116 of the aerosol holding chamber 112 and the attachment end 130 of the recirculation chamber 126 to the intermediate tube 118.

The inhaler 110 of FIGS. 1 and 2 has a plurality of one-way check valves therein in order to control the flow of air and/or medication through the device. The side elevation view in section of FIG. 2 illustrates the flow paths through the device, and the locations of the various check valves therein. The check valves may be of any suitable configuration, e.g., spring loaded ball check valves, spring loaded poppet valves, etc., but preferably comprise what are commonly known as membrane or "reed" type valves, i.e., a thin, flexible sheet of material secured to one side of an open frame, with the sheet freely flexing away from the frame as air (or other fluid) flows through the frame to push the sheet away from the frame, but sealing against fluid flow in the opposite direction as the flexible sheet is pushed against the frame by differential pressure. This type of valve, when incorporating a very thin, flexible sheet of rubber, vinyl, or similar material, is quite economical, reasonably durable, and operates very rapidly using very little differential air or fluid pressure.

Air is initially drawn into the aerosol holding chamber 112 through a pair of inlet check valves 136 installed in the side or top of the aerosol holding chamber 112 simultaneously with the injection of medication into the chamber 112 by means of the MDI or nebulizer N. The aerosol holding chamber inlet check valves 136 are oriented to permit air to flow into the aerosol holding chamber 112, while blocking outflow. Thus, in the event that pressure within the aerosol holding chamber 112 becomes higher than ambient, air (and medication) cannot escape through the inlet check valves 136. While two such inlet check valves 136 are illustrated in FIGS. 1 and 2, it should be noted that a single such valve, or more than two such valves, may be incorporated into the aerosol holding chamber 112.

Air and medication mixed therewith passes from the aerosol holding chamber 112 to the intermediate tube 118 and thence to the user interface device 124 (or other device) through an intermediate one-way check valve 138 installed at the outlet or delivery end 116 of the aerosol holding chamber 112. This intermediate valve 138 permits fluid flow from the holding chamber 112 into the intermediate tube 118, and thence into the mouthpiece 124 (or other device), while blocking flow in the reverse direction from the mouthpiece 124 back into the holding chamber 112.

Any air (and medication) exhaled by the user back into the mouthpiece 124 passes into the recirculation chamber 126 by way of the attachment end passage 130 thereof, which connects the recirculation chamber 126 to the intermediate tube 118. A recirculation check valve 140 is provided at the outlet end of the recirculation passage 134, where the recirculation passage 134 connects to the aerosol holding chamber 112, in order to permit exhaled air and medication to flow back into the aerosol holding chamber 112 for recycling while preventing flow from the holding chamber 112 directly into the recirculation chamber 126 through the recirculation passage 134. Alternatively, the recirculation check valve 140 may be installed in the attachment end 130 of the recirculation chamber 126, i.e., the inlet side or passage of the recirculation chamber 126. Such an alternative recirculation valve location is indicated as valve 140*a* in FIG. 2. Alternatively, the attachment end 130 of the recirculation chamber 126 may include two (or more) passages extending therefrom, with each passage including a separate one-way recirculation check valve 140*a*. It will be understood that it is not necessary to provide both recirculation valves 140 and 140*a*, as the inlet and outlet passages 130 and 134 of the recirculation chamber 126 comprise a plurality flow, so only a single recirculation valve 140 or 140*a* is required at some point in the inlet or outlet side of the recirculation chamber 126.

The above-described system is a one-way system, i.e., no outflow is permitted through any of the passages other than the mouthpiece 124 (or other user interface device). Accordingly, some means must be provided to vent the device in order to allow the user to exhale back into the device in order to recirculate air and medication for efficient reuse. This is provided by an outflow check valve 142 located in the distal end 132 of the recirculation chamber 126, along with an exhalation filter 144. The exhalation filter 144 is preferably an HME (Heat and Moisture Exchanger) type filter, i.e., activated charcoal capable of capturing medication in suspended vapor form, viruses, etc., or a HEPA (High Efficiency Particulate Air) filter with much the same capabilities. In any event, the exhalation filter 144 should be capable of preventing the escape of vaporized or nebulized medication from the recirculation chamber 126.

Figure 1A:
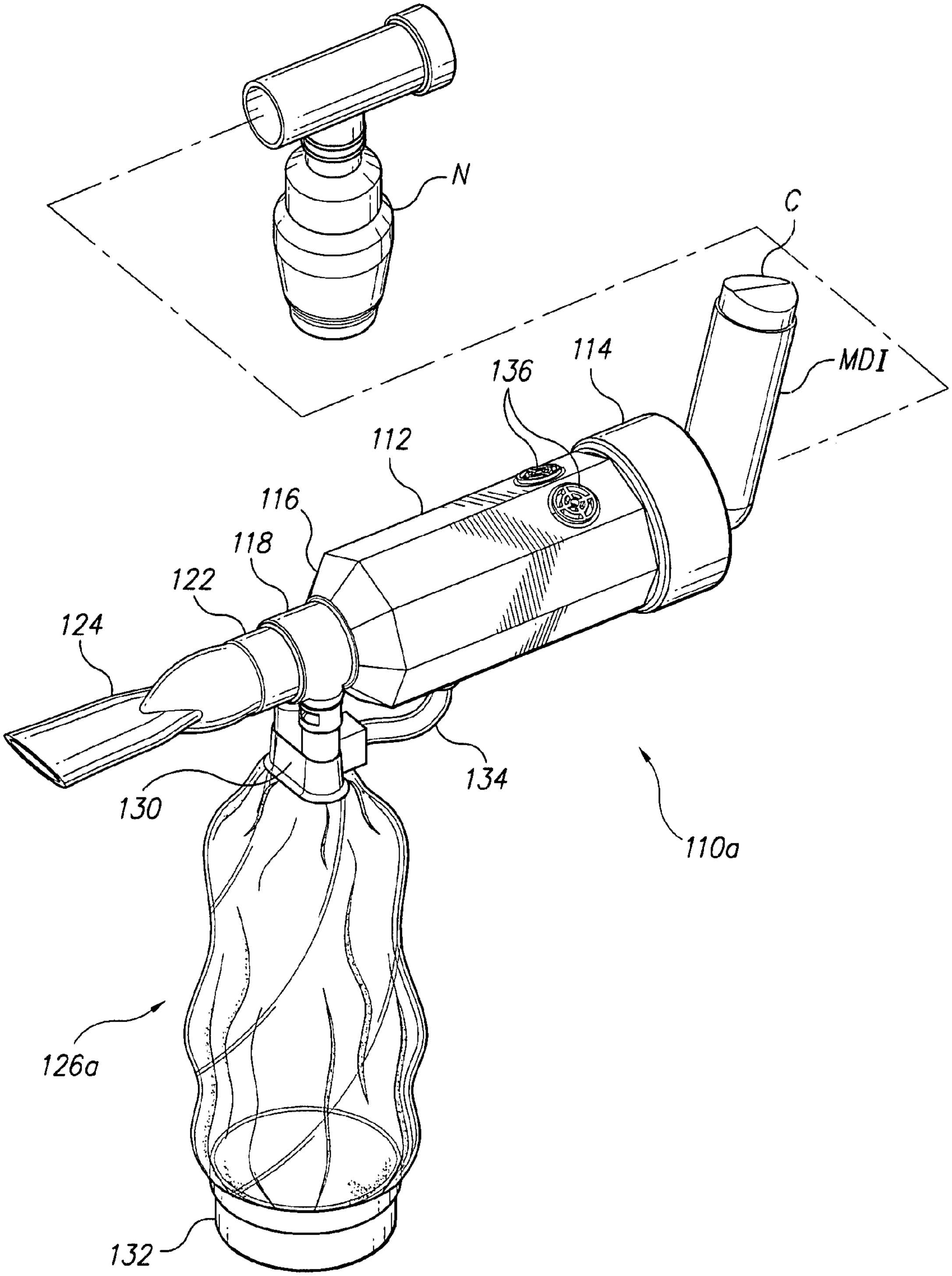
FIG. 1A is a perspective view of a modification of the inhaler of FIG. 1, wherein a flexible rebreather bag is substituted for the rigid rebreather chamber of FIG. 1.

FIG. 1A is a perspective view of an alternative inhaler for aerosol medication 110*a*, based upon the inhaler embodiment 110 of FIG. 1. The aerosol holding chamber 112 with its provision for the attachment of a nebulizer N or MDI, mouthpiece 124, and various check valves, are identical in both the inhaler 110 of FIGS. 1 and 2 and the inhaler 110*a* of FIG. 1A. However, the inhaler 110*a* of FIG. 1A includes a flexible recirculation bag 126*a*, rather than the rigid recirculation chamber 126 of the inhaler 110. The flexible recirculation bag 126*a* includes an outflow check valve and exhalation filter in its distal end 132, which are substantially identical to the outflow check valve 142 and filter 144 of the rigid recirculation chamber 110 of FIGS. 1 and 2. The flexible recirculation bag 126*a* of the embodiment 110*a* of FIG. 1A provides advantages in the compact storage of the inhaler 110*a*, as the flexible bag 126*a* may be collapsed for storage of the device.

Figure 3:
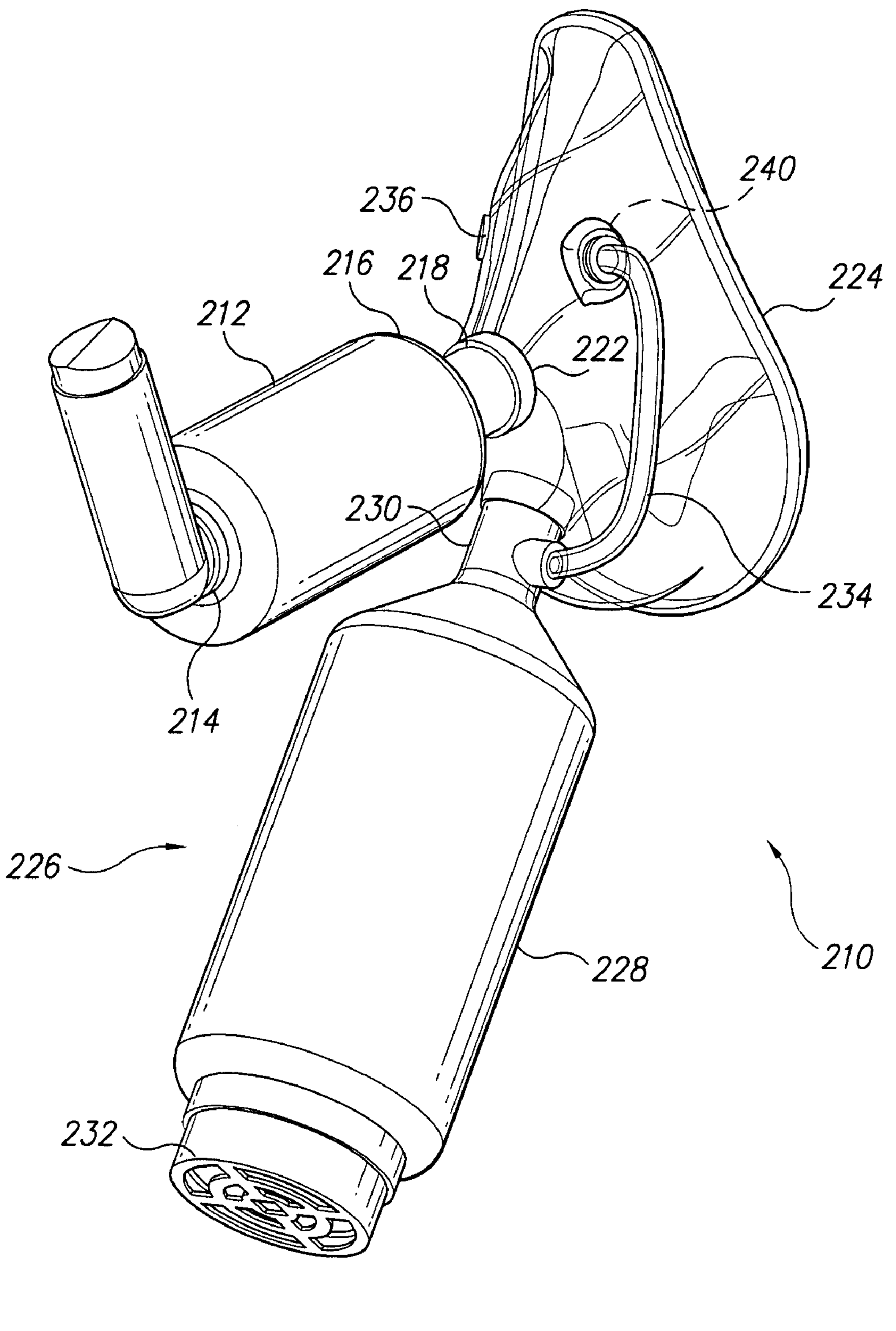
FIG. 3 is a perspective view of a second embodiment of an inhaler for aerosol medication according to the present invention, wherein the device includes a face mask.
Figure 4:
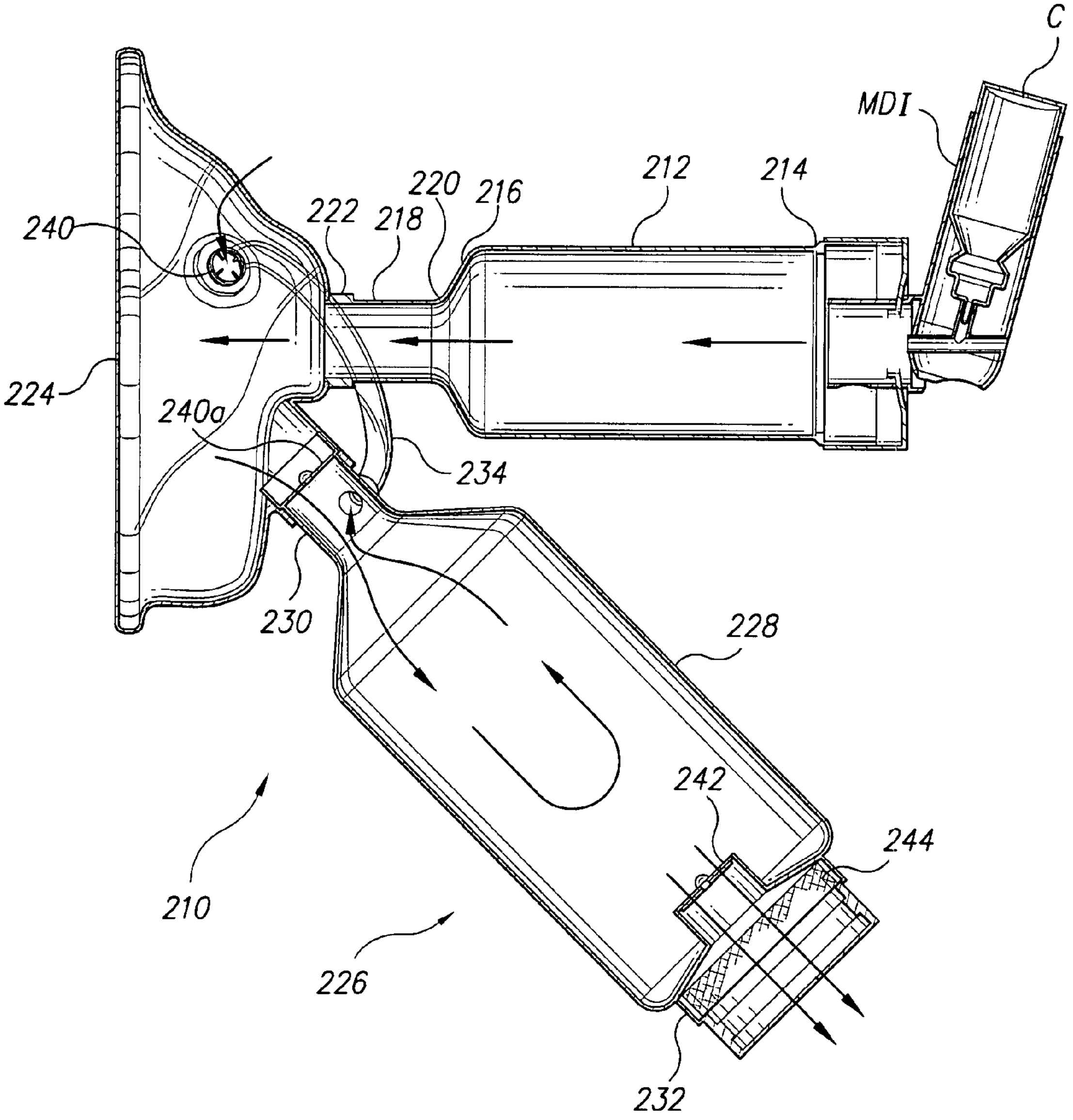
FIG. 4 is a right side elevation view in section of the inhaler of FIG. 3, showing various internal details thereof and the flow path therethrough.

FIGS. 3 and 4 respectively show a perspective view and a right side elevation view in section of a second embodiment of an inhaler for aerosol medication, designated as 210 in the drawings. The inhaler 210 includes many of the same basic components as the inhaler 110 of FIGS. 1 and 2, with equivalent components having three digit reference numerals with the same second and third digits as those used for the equivalent components of the inhaler 110. The inhaler 210 includes an aerosol holding chamber 212 having a medication dispenser attachment end 214 and a delivery end 216 opposite the dispenser attachment end. The dispenser attachment end 214 may accept a conventional metered dose inhaler (MDI) with its manually operated medication container or canister C, or alternatively a nebulizer N may be attached to the medication dispenser attachment end 214 of the aerosol holding chamber 212, as shown with the inhaler embodiment 110 of FIG. 1. The aerosol holding chamber 212 may have a round cross section, or any other practicable cross-sectional shape.

An intermediate tube 218 extends from the delivery end 216 of the chamber 212, with the intermediate tube having a first end 220 attached to the delivery end 216 of the chamber 212 and an opposite user interface device attachment end 222 extending therefrom. A user interface device, e.g., a face mask 224 as shown in FIGS. 3 and 4, may be removably or permanently affixed to the user interface device attachment end 222 of the intermediate tube 218. The use of a face mask 224, rather than a mouthpiece, as the user interface device is the primary difference between the inhaler 110 of FIGS. 1 and 2 and inhaler 210 of FIGS. 3 and 4. However, there are other differences in the arrangement of similar components, and the possible omission or addition of various valves.

Recirculation chamber 226 has a rigid shell 228 with an attachment end 230 connected to and communicating with the face mask 224, and an opposite, distal end 232. The recirculation chamber 226 may have any practicable geometric cross-sectional shape or configuration. An additional recirculation passage 234 extends from the attachment end 230 of the recirculation chamber 226 to an inlet in the face mask 224, with the recirculation passage 234 communicating with the intermediate tube 218 of the embodiment 210 of FIGS. 3 and 4 by means of the connection of both the attachment end 230 of the recirculation chamber 226 (with the recirculation passage 234 extending therefrom) to the face mask 224 and the attachment of the intermediate tube 218 to the face mask 224.

The inhaler 210 of FIGS. 3 and 4 further includes a plurality of one-way check valves therein in order to control the flow of air and/or medication through the device. The side elevation view in section of FIG. 4 illustrates the flow paths through the device, and the locations of the various check valves therein. The check valves may be of any suitable configuration, as described further above in the description of the check valves for the embodiment 110 of FIGS. 1 and 2.

It will be noted that the inhaler 210 of FIGS. 3 and 4 does not include any air inlet valves in the aerosol holding chamber 212, unlike the chamber 112 of the embodiment of FIGS. 1 and 2. Rather, inhalation through the mask 224 draws ambient air in through a one-way inlet check valve 236 disposed within the face mask 224. This check valve 236 is located laterally, symmetrically from the mask connection for the recirculation passage 234, but the edge of the valve 236 may be seen in FIG. 3. The face mask inlet check valve 236 is oriented to permit air to flow into the face mask 224 while blocking outflow. Alternatively, two or more such inlet check valves 236 could be installed in the mask 224 to reduce restriction in the inflow of air to the mask. Such multiple inlet check valves are indicated as valves 136 in the inhaler 110 embodiment of FIGS. 1 and 2, valves 336 in the inhaler embodiment 310 of FIGS. 5 through 8, and valves 436 in the inhaler embodiment 410 of FIGS. 9 through 12.

Some means must be provided for mixing ambient air with the medication delivered to the aerosol holding chamber 212 by the MDI or nebulizer N, in view of the fact that the inhaler embodiment 210 does not include any inlet valves communicating directly with the interior of the holding chamber 212. Accordingly, the inhaler embodiment 212 does not include any form of intermediate check valve between the holding chamber 112 and the intermediate passage 218 to the mask 224. Thus, the user may draw in ambient air through the mask inlet check valve 236 and exhale freely back through the intermediate tube 218 into the aerosol holding chamber 212 to mix the vaporized medication from the MDI or nebulizer N with exhaled air. Alternatively, an inlet check valve(s) could be provided in the aerosol holding chamber 212 and the inlet check valve of the face mask 224 could be eliminated, if an intermediate check valve were to be installed within the intermediate tube of the embodiment 210 of FIGS. 3 and 4.

Any air (and medication) exhaled by the user back into the face mask 224 passes either into the aerosol holding chamber 212 as described above, or into the recirculation chamber 226 by way of the attachment end passage 230 thereof connecting the recirculation chamber to the face mask 224. A recirculation check valve 240 may be provided at the outlet end of the recirculation passage 234 where the recirculation passage 234 connects to the face mask 224 to permit exhaled air and medication to flow back into the aerosol holding chamber 212 for recycling while preventing backflow through the recirculation passage 234. It will be understood that the recirculation valve 240 is not absolutely necessary in the configuration illustrated in FIG. 4, with its lack of a check valve between the face mask 224 and the aerosol holding chamber 212. The recirculation check valve 240 may only be required when one or more inlet valves are provided in the aerosol holding chamber 212, rather than in the face mask 224, and an intermediate check valve is installed between the holding chamber 212 and the face mask 224. Another recirculation check valve 140*a* may be installed in the attachment end 230 of the recirculation chamber 226, i.e., the inlet side or passage of the recirculation chamber 226 where it joins to the face mask 224. The installation of the two recirculation check valves 140 and 140*a* ensures that flow will pass into the recirculation chamber 226 through the attachment end 230 thereof and exit through the recirculation passage 234, as indicated by the flow arrows in FIG. 4.

The above-described system is a one-way system, i.e., no outflow is permitted through any of the passages other than the face mask 224 (or other user interface device). Accordingly, some means must be provided to vent the device in order to allow the user to exhale back into the device in order to recirculate air and medication for efficient reuse. This is provided by an outflow check valve 242 located in the distal end 232 of the recirculation chamber 226, along with an exhalation filter 244 of the general type and properties described further above for the exhalation filter 144 of the inhaler embodiment 110 of FIGS. 1 and 2.

Figure 3A:
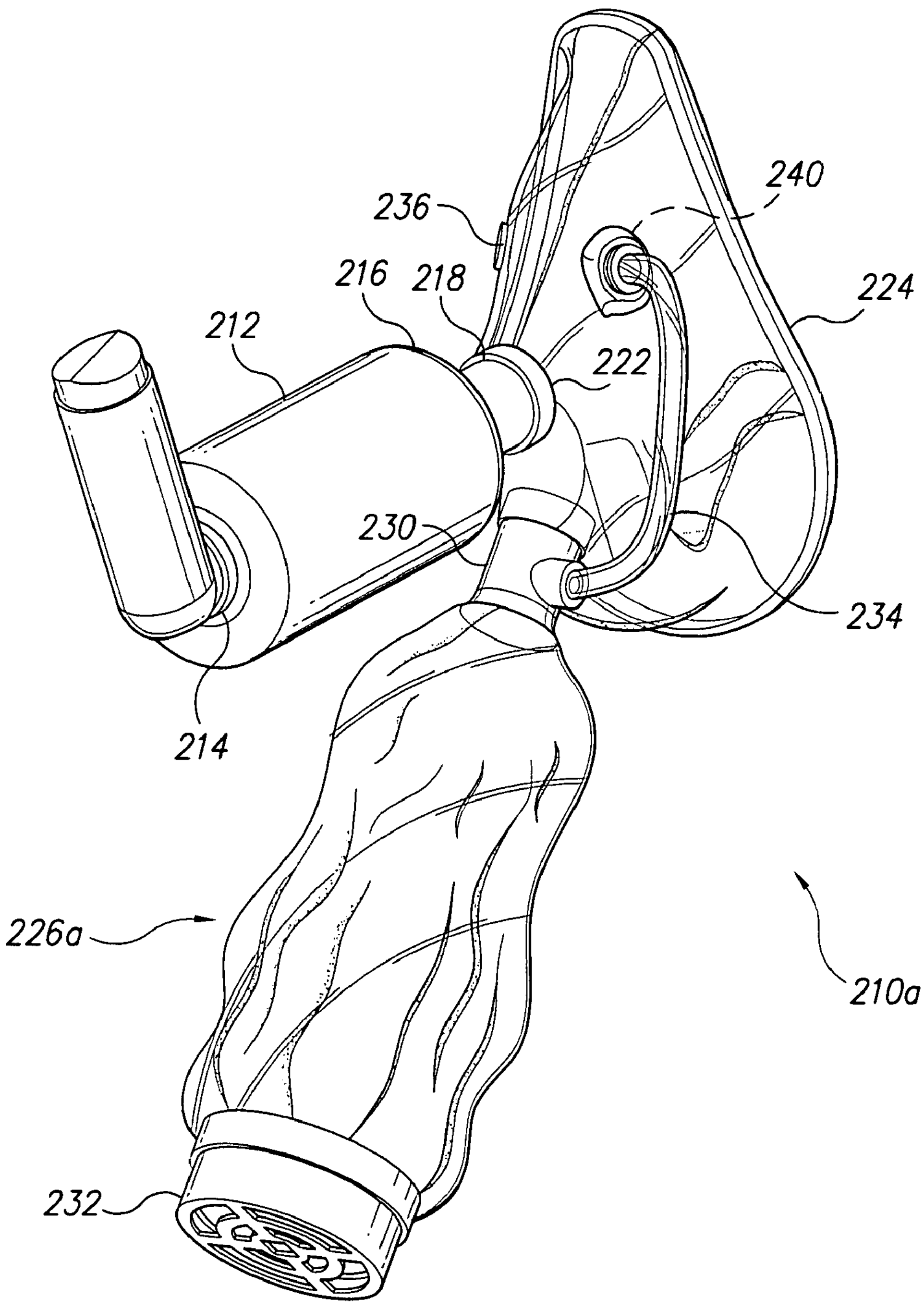
FIG. 3A is a perspective view of a modification of the inhaler of FIG. 3, wherein a flexible rebreather bag is substituted for the rigid rebreather chamber of FIG. 3.

FIG. 3A is a perspective view of an alternative inhaler for aerosol medication 210*a*, based upon the inhaler embodiment 210 of FIGS. 3 and 4. The aerosol holding chamber 212 with its provision for the attachment of a nebulizer N or MDI, face mask 224, and various check valves, are identical in both the inhaler 210 of FIGS. 3 and 4 and the inhaler 210*a* of FIG. 3A. However, the inhaler 210*a* of FIG. 3A includes a flexible recirculation bag 226*a* substantially identical to the flexible recirculation bag 126*a* of FIG. 1A, rather than the rigid recirculation chamber 226 of the inhaler 210. The flexible recirculation bag 226*a* includes an outflow check valve and exhalation filter in its distal end 232, which are substantially identical to the outflow check valve 142 and filter 144 of the rigid recirculation chamber embodiment 110 of FIGS. 1 and 2, and are also incorporated in the embodiment 210 of FIGS. 3 and 4 as valve 242 and filter 244. The flexible recirculation bag 226*a* of the inhaler 210*a* of FIG. 3A provides advantages in the compact storage of the inhaler 210*a*, as the flexible bag 226*a* may be collapsed for storage of the device.

FIGS. 5 through 8 illustrate a third embodiment of the inhaler for aerosol medication, designated as inhaler 310. The inhaler 310 includes many of the same basic components as the inhaler 110 of FIGS. 1 and 2 and inhaler 210 of FIGS. 3 and 4, with equivalent components having three digit reference numerals with the same second and third digits as those used for the equivalent components of the inhalers 110 and 210. The inhaler 310 includes a telescoping aerosol holding chamber 312 having an outer portion 312*a* with a medication dispenser attachment end 314, an inner portion 312*b* with a delivery end 316 opposite the medication dispenser attachment end 314, and a selectively closable cover 317 extending from the outer portion 312*a*. The dispenser attachment end 314 may accept a conventional metered dose inhaler (MDI) with its manually operated medication container or canister C, or alternatively a nebulizer N may be attached to the medication dispenser attachment end 314 of the aerosol holding chamber 312, as shown with the inhaler embodiment 110 of FIG. 1. The telescoping aerosol holding chamber 312 may have a rectangular cross section as shown, or any other practicable cross-sectional shape.

An intermediate tube 318 extends from the delivery end 316 of the chamber 312, with the intermediate tube having a first end 320 attached to the delivery end 316 of the chamber 312 and an opposite user interface device attachment end 322 extending therefrom. A user interface device, e.g., a mouthpiece 124 as shown in FIGS. 1 and 2 or a face mask 224 as shown in FIGS. 3 and 4, may be removably or permanently affixed to the user interface device attachment end 322 of the intermediate tube 318.

A collapsible bellows recirculation chamber 326 has an attachment end 330 connected to and communicating with the intermediate tube 318, and a distal end 332 opposite the attachment end. The recirculation chamber 326 may have any practicable geometric cross-sectional shape or configuration, with the cross-sectional shape being limited by the need to collapse the chamber 326 for compact storage. An additional recirculation passage 334, shown in FIGS. 6 and 8, extends from the attachment end 330 of the recirculation chamber 326 to the inlet end 316 of the inner portion 312*b* of the aerosol holding chamber 312, with the recirculation passage 334 communicating with the intermediate tube 318 of the inhaler 310 of FIGS. 5 through 8 by means of the connection of the attachment end 330 of the recirculation chamber 326 (with the recirculation passage 334 extending therefrom) to the delivery end 316 of the inner portion 312*b* of the aerosol holding chamber 312 and the attachment of the chamber 312 to the intermediate tube 318.

Figure 6:
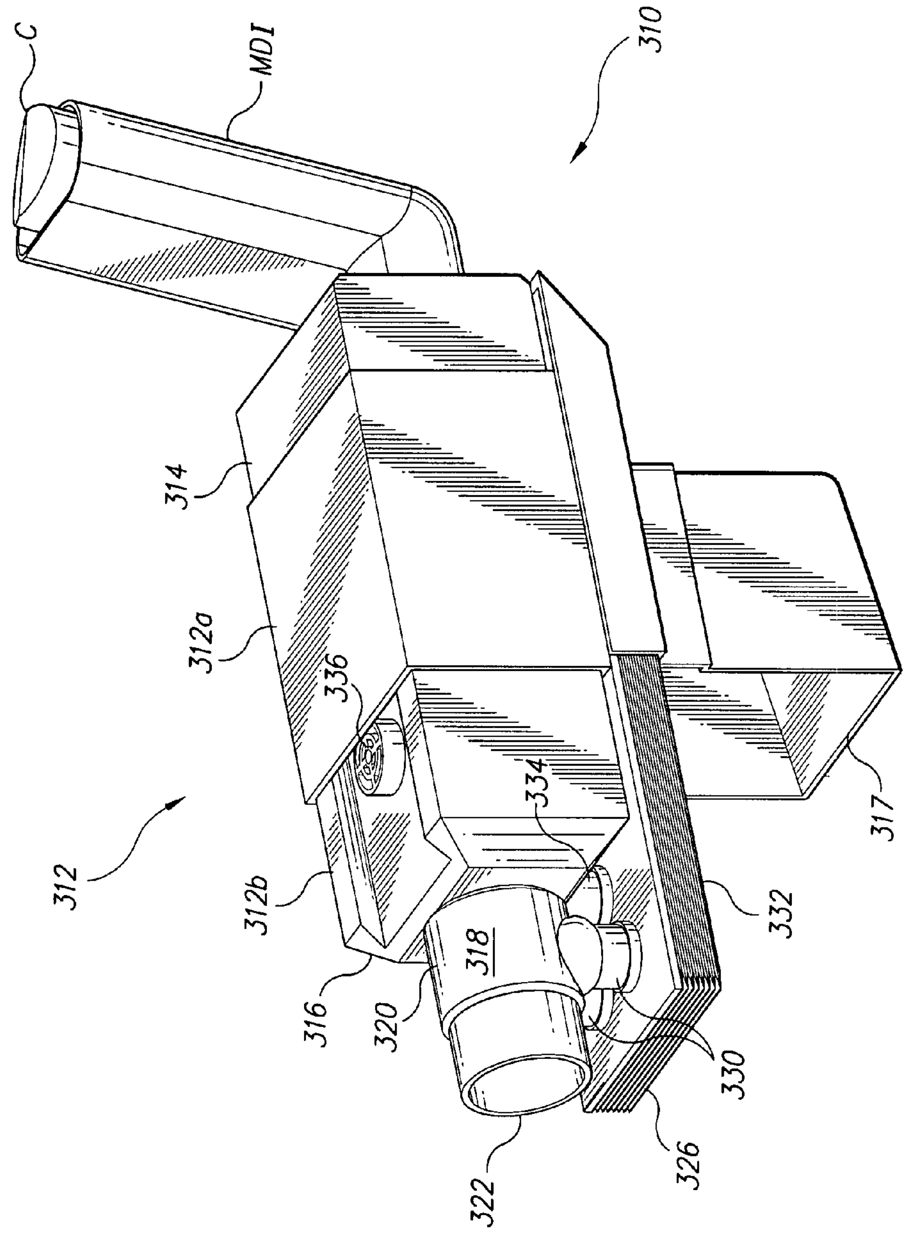
FIG. 6 is a perspective view of the inhaler of FIG. 5, showing the recirculation bellows in a collapsed configuration.
Figure 7:
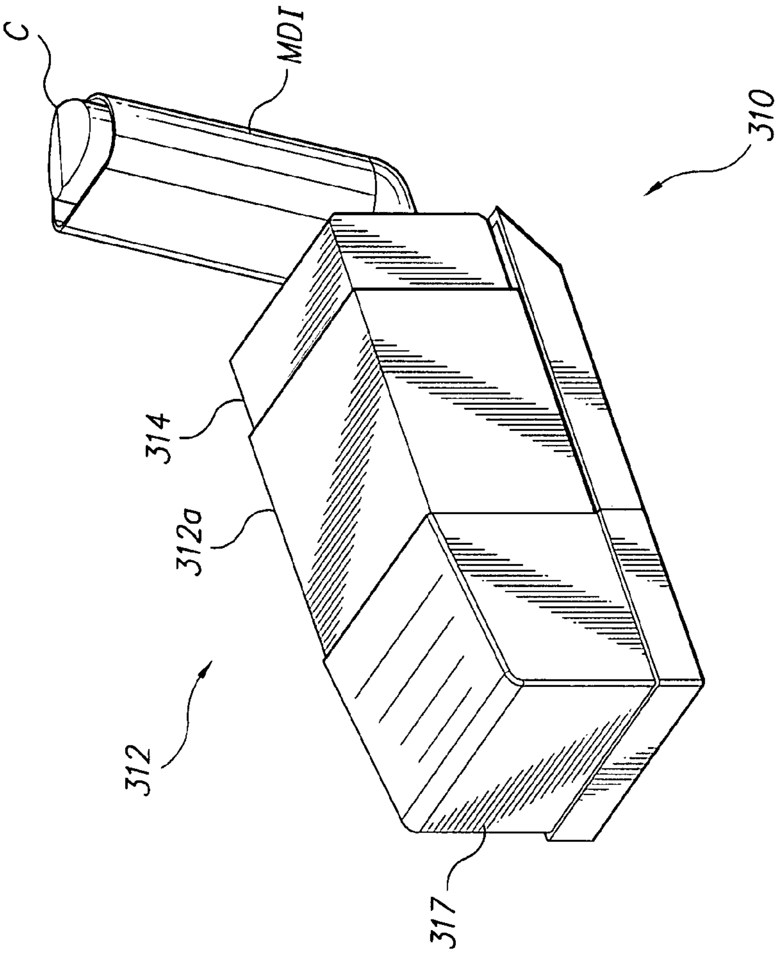
FIG. 7 is a perspective view of the inhaler of FIGS. 5 and 6, showing the device completely folded and closed for storage.
Figure 8:
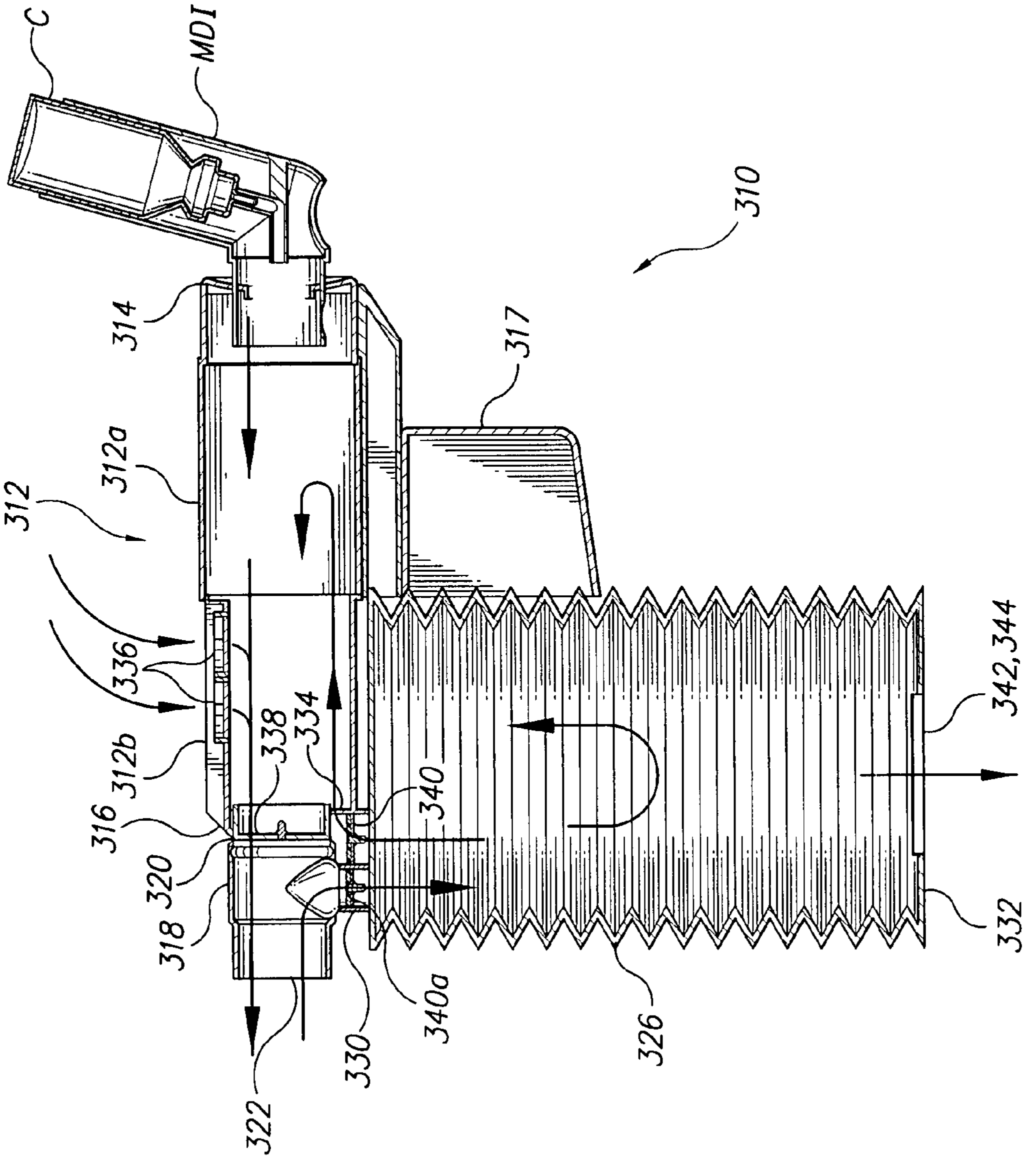
FIG. 8 is a right side elevation view in section of the inhaler of FIG. 5 in operation, showing various internal details thereof and the flow path therethrough.
Figure 9:
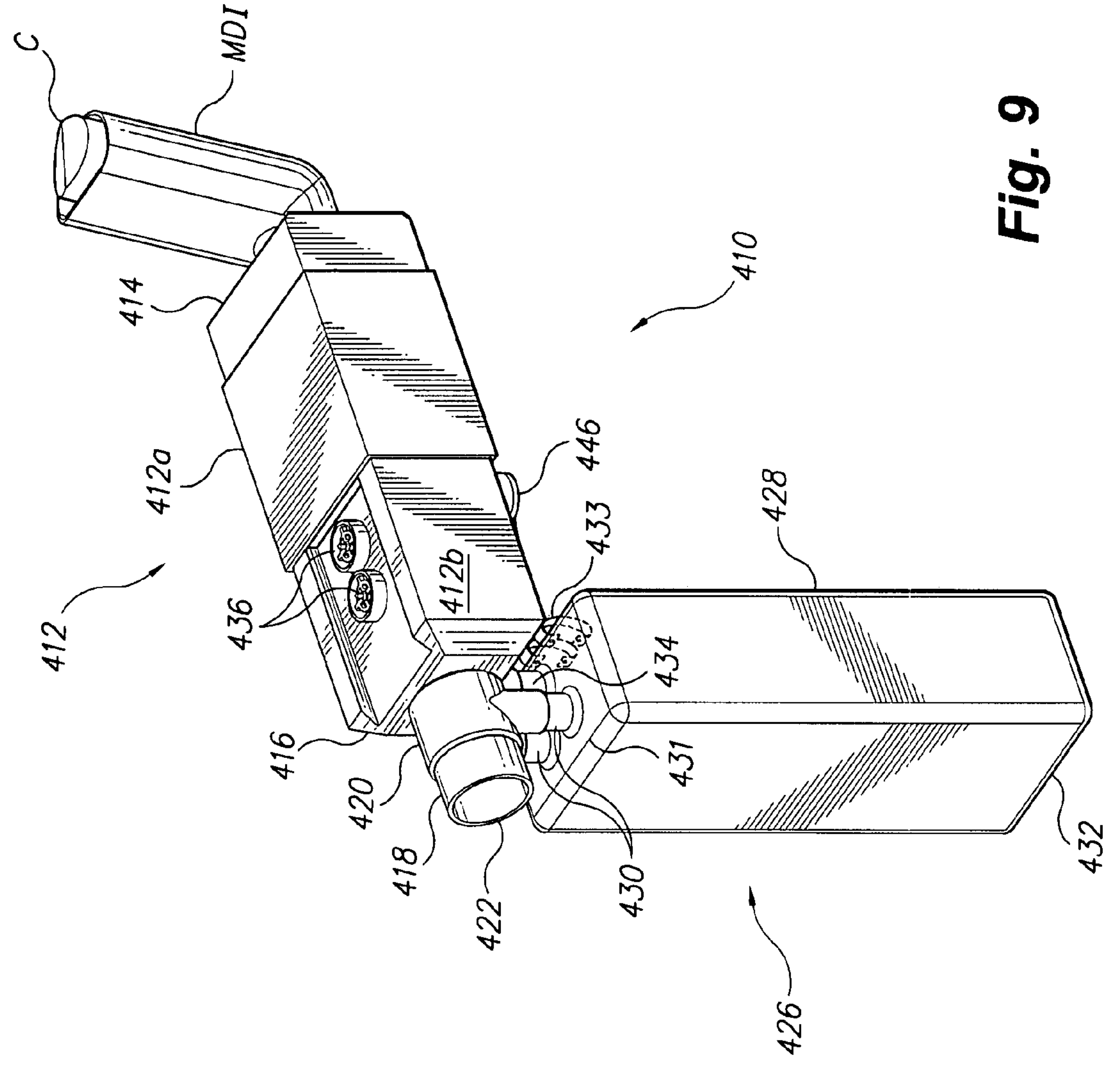
FIG. 9 is a perspective view of a fourth embodiment of an inhaler for aerosol medication according to the present invention, wherein the holding chamber may be stored within the recirculation chamber.

The inhaler 310 of FIGS. 5 through 8 further includes a plurality of one-way check valves therein in order to control the flow of air and/or medication through the device. The side elevation view in section of FIG. 8 illustrates the flow paths through the device and the locations of the various check valves therein. The check valves may be of any suitable configuration, as described further above in the description of the check valves for the embodiment 110 of FIGS. 1 and 2.

Figure 5:
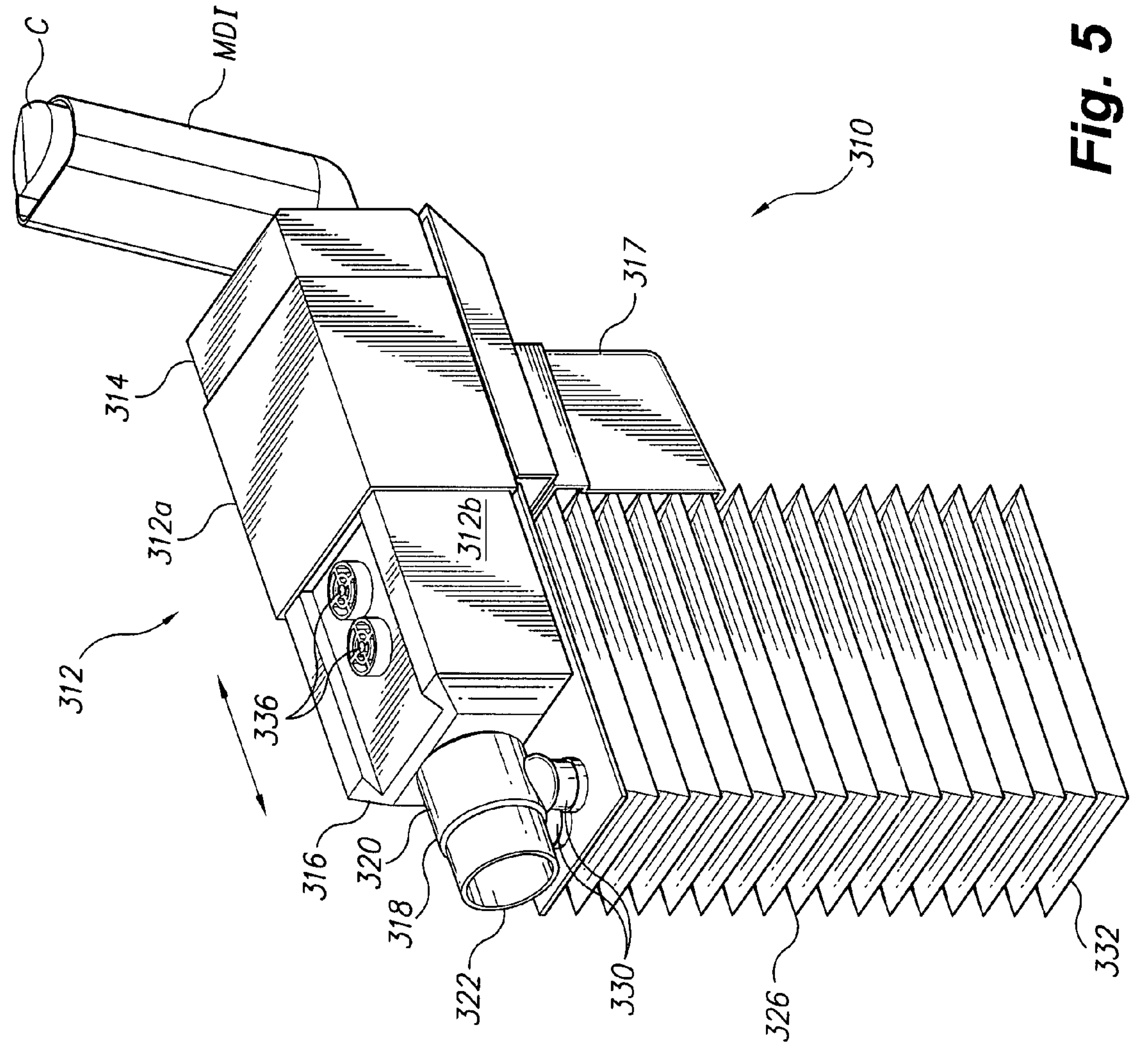
FIG. 5 is a perspective view of a third embodiment of the inhaler for aerosol medication according to the present invention, wherein the recirculation chamber comprises a collapsible bellows for compact storage.

Air is initially drawn into the aerosol holding chamber 312 through a pair of inlet check valves 336 installed in the side or top of the aerosol holding chamber 312, particularly in the top of the inner portion 321*b* thereof, simultaneously with the injection of medication into the chamber 312 by means of the MDI or nebulizer N. The aerosol holding chamber inlet check valves 336 are oriented to permit air to flow into the aerosol holding chamber 312 while blocking outflow. Thus, in the event that pressure within the aerosol holding chamber 312 becomes higher than ambient, air (and medication) cannot escape through the inlet check valves 336. While two such inlet check valves 336 are illustrated in FIGS. 5 and 8, it should be noted that a single such valve, or more than two such valves, may be incorporated as desired.

Air and medication mixed therewith passes from the aerosol holding chamber 312 to the intermediate tube 318 and thence to the user interface device (e.g., the mouthpiece 124 of FIGS. 1 and 2, or the face mask 224 of FIGS. 3 and 4) through an intermediate one-way check valve 338 installed at the outlet or delivery end 316 of the aerosol holding chamber 312. This intermediate valve 338 permits fluid flow from the holding chamber 312 into the intermediate tube 318 and thence into the user interface device, while blocking flow in the reverse direction from the user interface device back into the holding chamber 312.

Any air (and medication) that is exhaled by the user back through the user interface device passes into the recirculation chamber 326 by way of the attachment end passage(s) 330 thereof connecting the recirculation chamber to the intermediate tube 318. A recirculation check valve 340 is provided within the recirculation passage 334 where the recirculation passage 334 connects to the aerosol holding chamber 312 (or more precisely, to its inner portion 312*b* adjacent the delivery end thereof) to permit exhaled air and medication to flow back into the aerosol holding chamber 312 for recycling while preventing flow from the holding chamber 312 directly into the recirculation chamber 326 through the recirculation passage 334. Alternatively, the recirculation check valve may be installed in the attachment end passage(s) 330 of the recirculation chamber 326, i.e., the inlet side or passage of the recirculation chamber 326. Such an alternative recirculation valve location is indicated as valve 340*a* in FIG. 8. Alternatively, the attachment end 330 of the recirculation chamber 326 may include two (or more) passages extending therefrom, with each passage including a separate one-way recirculation check valve 340*a*. It will be understood that it is not necessary to provide both recirculation valves 340 and 340*a*, as the inlet and outlet passages 330 and 334 of the recirculation chamber 326 comprise a plurality flow, so that only a single recirculation valve 340 or 340*a* is required at some point in the inlet or outlet side of the recirculation chamber 326.

The above-described system is a one-way system, i.e., no outflow is permitted through any of the passages other than the intermediate tube 318 and any user interface device connected thereto. Accordingly, some means must be provided to vent the device in order to allow the user to exhale back into the device in order to recirculate air and medication for efficient reuse. This is provided by an outflow check valve 342 located in the distal end 332 of the recirculation chamber 326, along with an exhalation filter 344 of the general type and properties described further above for the exhalation filter 144 of the inhaler embodiment 110 of FIGS. 1 and 2. The distal end 132 and 232 of the embodiments 110 and 210, with their respective exhalation check valves 142 and 242 and filters 144 and 244 have been shown respectively in FIGS. 2 and 4 and discussed further above, and are indicated only generally in the cross-sectional side elevation view of FIG. 8.

FIGS. 5 through 7 also illustrate the general progression in converting the inhaler 310 from its deployed to its collapsed or stowed configuration for compact storage. The device 310 is shown fully deployed with the bellows recirculation chamber 326 fully extended in FIG. 5 and ready for use, with perhaps the only additional component needed being the mouthpiece 124 of the embodiment of FIGS. 1 and 2 or the face mask 224 of the embodiment of FIGS. 3 and 4. The inhaler 310 is collapsed for storage by first folding the collapsible bellows recirculation chamber 326, as shown in FIG. 6. Normally, a cap or closure (not shown) would be placed over the otherwise exposed user interface connection end 322 of the intermediate tube 318 in order to assure that all vapor contained within the inhaler device 310 remains within the device. Any air and/or medication vapor contained within the expanded bellows chamber 326 is forced through the outflow check valve and exhalation filter assembly 342, 344 as the chamber 326 is collapsed, with any medication and/or other large molecule particulate matter being captured in the exhalation filter 344.

When the bellows recirculation chamber 326 has been completely collapsed, as shown in FIG. 6, the inner portion or sleeve 312*b* of the aerosol holding chamber 312 is telescoped into the outer portion or sleeve 312*a* of the holding chamber. Air and/or vapor, etc., captured within the aerosol holding chamber 312 as it is collapsed is forced from the holding chamber 312 into the intermediate tube 318 through the intermediate check valve 338, and thence into the collapsed bellows recirculation chamber 326 through the recirculation check valve 340*a* and out the outflow check valve and filter 342, 344. Once this has been completed, the hinged cover or cap 317 is swung upwardly to cover the otherwise protruding intermediate tube 318 and its user interface connector end 322 to completely enclose the collapsed recirculation chamber 326, intermediate tube 318, and inner sleeve portion 312*b* of the aerosol holding chamber 312, as shown in FIG. 7. The MDI or nebulizer N may be disconnected at this point, if so desired, and stored for future use.

FIGS. 9 through 12 illustrate a fourth embodiment of an inhaler for aerosol medication, designated as inhaler 410. The inhaler 410 includes many of the same basic components as the inhaler 110 of FIGS. 1 and 2, inhaler 210 of FIGS. 3 and 4, and inhaler 310 of FIGS. 5 through 8, with equivalent components having three digit reference numerals with the same second and third digits as those used for the equivalent components of the inhalers 110, 210, and 310. The inhaler 410 includes a telescoping aerosol holding chamber 412 having an outer portion 412*a* with a medication dispenser attachment end 414, and an inner portion 412*b* with a delivery end 416 opposite the medication dispenser attachment end 414. The dispenser attachment end 414 may accept a conventional metered dose inhaler (MDI) with its manually operated medication container or canister C, or, alternatively, a nebulizer N may be attached to the medication dispenser attachment end 414 of the aerosol holding chamber 412, as shown with the inhaler 110 of FIG. 1. The telescoping aerosol holding chamber 412 may have a rectangular cross section as shown, or any other practicable cross-sectional shape.

An intermediate tube 418 extends from the delivery end 416 of the chamber 412, with the intermediate tube having a first end 420 attached to the delivery end 416 of the chamber 412 and an opposite user interface device attachment end 422 extending therefrom. A user interface device, e.g., a mouthpiece 124 as shown in FIGS. 1 and 2 or a face mask 224 as shown in FIGS. 3 and 4, may be removably or permanently affixed to the user interface device attachment end 422 of the intermediate tube 418.

A combination recirculation and aerosol holding chamber storage chamber 426 (hereinafter called the "combination chamber 426") has a rigid shell 428 with an attachment end or attachment end passage(s) 430 removably connected and communicating with the intermediate tube 418, a distal end 432 opposite the attachment end or attachment end passage(s) 430, and a selectively openable cover 431 disposed upon the attachment end and secured thereto by hinges 433. The combination chamber 426 may have any practicable geometric cross-sectional shape or configuration, with the cross-sectional shape being limited by the need for the combination chamber 426 to enclose the aerosol holding chamber 412 for compact storage. An additional recirculation passage 434 extends from the attachment end 430 of the combination chamber 426 to the inlet end 416 of the inner portion 412*b* of the aerosol holding chamber 412, the recirculation passage 434 communicating with the intermediate tube 418 of the inhaler 410 of FIGS. 9 through 12 by means of the connection of the attachment end 430 of the combination chamber 426 (with the recirculation passage 434 extending therefrom) to the delivery end 416 of the inner portion 412*b* of the aerosol holding chamber 412 and the attachment of the chamber 412 to the intermediate tube 418.

Figure 12:
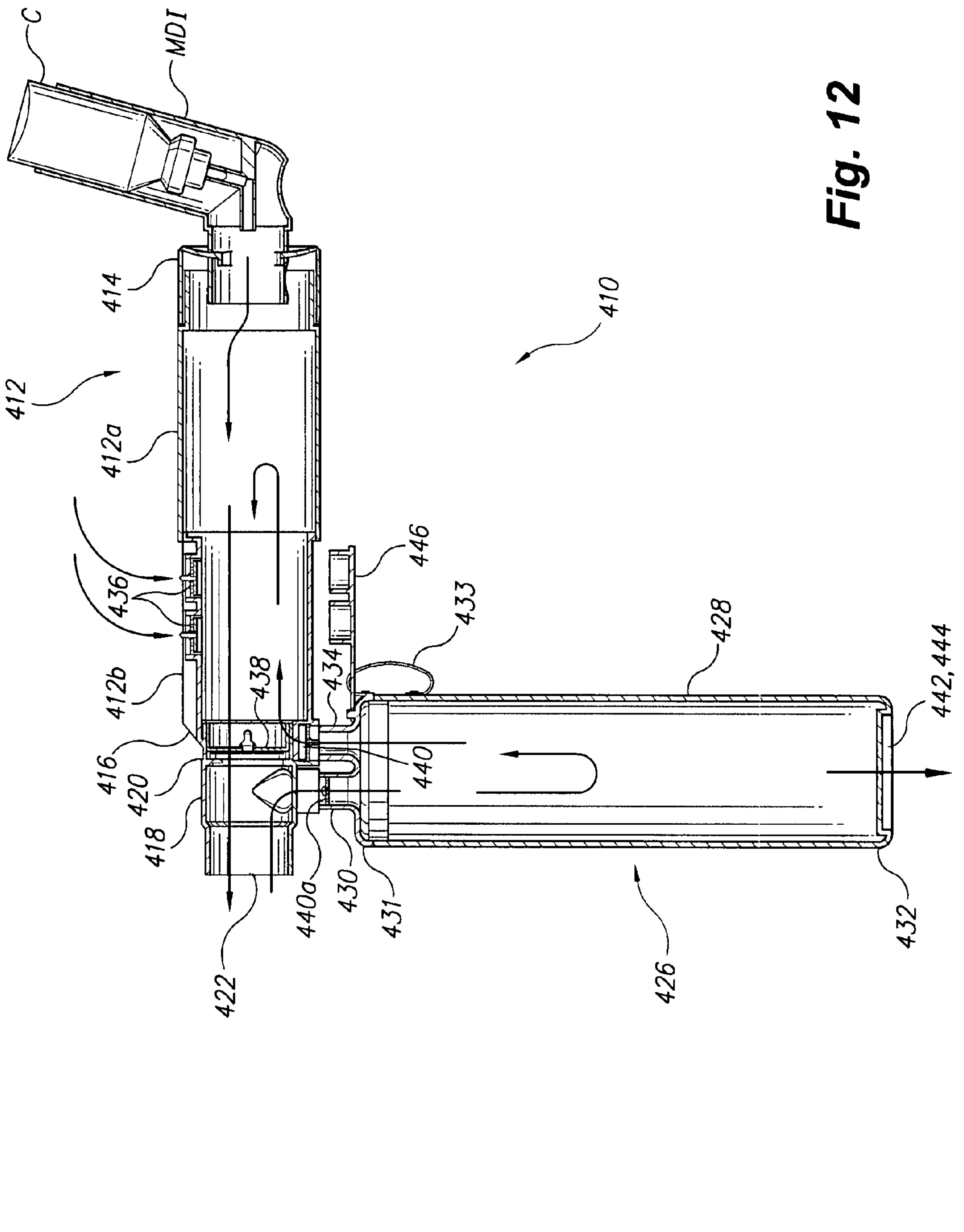
FIG. 12 is a right side elevation view in section of the inhaler of FIG. 9 in operation, showing various internal details thereof and the flow path therethrough.

The inhaler 410 of FIGS. 9 through 12 further includes a plurality of one-way check valves therein, in order to control the flow of air and/or medication through the device. The side elevation view in section of FIG. 12 illustrates the flow paths through the device, and the locations of the various check valves therein. The check valves may be of any suitable configuration, as described further above in the description of the check valves for the embodiment 110 of FIGS. 1 and 2.

Air is initially drawn into the aerosol holding chamber 412 through a pair of inlet check valves 436 installed in the side or top of the aerosol holding chamber, particularly in the top of the inner portion 421*b* thereof, simultaneously with the injection of medication into the chamber 412 by means of the MDI or nebulizer N. The aerosol holding chamber inlet check valves 436 are oriented to permit air to flow into the aerosol holding chamber 412, while blocking outflow. Thus, in the event that pressure within the aerosol holding chamber 412 becomes higher than ambient, air (and medication) cannot escape through the inlet check valves 436. While two such inlet check valves 436 are illustrated in the inhaler embodiment 410 of FIGS. 9 through 12, it should be noted that a single such valve, or more than two such valves, may be incorporated as desired.

Air and medication mixed therewith passes from the aerosol holding chamber 412 to the intermediate tube 418 and thence to the user interface device (e.g., the mouthpiece 124 of FIGS. 1 and 2, or the face mask 224 of FIGS. 3 and 4) through an intermediate one-way check valve 438 installed at the outlet or delivery end 416 of the aerosol holding chamber 412. This intermediate valve 438 permits fluid flow from the holding chamber 412 into the intermediate tube 418 and thence into the user interface device, while blocking flow in the reverse direction from the user interface device back into the holding chamber 412.

Any air (and medication) exhaled by the user back through the user interface device passes into the recirculation chamber 426 by way of the attachment end passage(s) 430 thereof connecting the recirculation chamber to the intermediate tube 418. A recirculation check valve 440 is provided within the recirculation passage 434 where the recirculation passage 434 connects to the aerosol holding chamber 412 (or more precisely, to its inner portion **412*b* adjacent the delivery end thereof), to permit exhaled air and medication to flow back into the aerosol holding chamber 412 for recycling while preventing flow from the holding chamber 412 directly into the recirculation chamber 426 through the recirculation passage 434. Alternatively, the recirculation check valve may be installed in the attachment end passage(s) 430 of the recirculation chamber 426, i.e., the inlet side or passage of the recirculation chamber 426. Such an alternative recirculation valve location is indicated as valve 440*a* in FIG. 12. Alternatively, the attachment end cover 431 of the recirculation chamber 426 may include two (or more) passages 430 extending therefrom, with each including a separate one way recirculation check valve 440*a*. It will be understood that it is not necessary to provide both recirculation valves 440 and 440*a*, as the inlet and outlet passages 430 and 434 of the recirculation chamber 426 comprise a plurality flow, so that only a single recirculation valve 440 or 440*a* may be required at some point in the inlet or outlet side of the recirculation chamber 426**.

The above-described system is a one-way system, i.e., no outflow is permitted through any of the passages other than the intermediate tube 418 and any user interface device connected thereto. Accordingly, some means must be provided to vent the device, in order to allow the user to exhale back into the device in order to recirculate air and medication for efficient reuse. This is provided by an outflow check valve 442 located in the distal end 432 of the recirculation chamber 426, along with an exhalation filter 444 of the general type and properties described further above for the exhalation filter 144 of the inhaler embodiment 110 of FIGS. 1 and 2. The distal end 132 and 232 of the embodiments 110 and 210, with their respective exhalation check valves 142 and 242 and filters 144 and 244, have been shown in FIGS. 2 and 4 and discussed further above, and are indicated only generally in the cross-sectional side elevation view of FIG. 12.

FIGS. 8 through 12 also illustrate the general progression in converting the inhaler 410 from its deployed to its collapsed or stowed configuration for compact storage. The device 410 is shown fully deployed with the rigid combination chamber 426 connected to the intermediate tube 418 in FIG. 5 and ready for use, with perhaps the only additional component needed being the mouthpiece 124 of the embodiment of FIGS. 1 and 2 or the face mask 224 of the embodiment of FIGS. 3 and 4. The inhaler 410 is collapsed for storage by first telescoping the inner portion or sleeve **412*b* of the aerosol holding chamber 412 the outer portion or sleeve 412*a* of the holding chamber 412. Air and/or vapor, etc., captured within the aerosol holding chamber 412 as it is collapsed is forced from the holding chamber 412 into the intermediate tube 418 through the intermediate check valve 438, and thence into the combination chamber 426 through the recirculation check valve 440*a* and out the outflow check valve and filter 442, 444. Normally, a cap or closure (not shown) would be placed over the otherwise exposed user interface connection end 422 of the intermediate tube 418 in order to assure that all vapor contained within the inhaler device 410** remains within the device.

Once this has been accomplished, the combination chamber 426 is disconnected from its connections to the intermediate tube 418 and delivery end 416 of the aerosol holding chamber 412 by unplugging the attachment end passages 430 and recirculation passage 434. This may allow any vapor within the combination chamber 426 to escape, so that it is best to accomplish this step in a location where the release of any vapors can do no harm. Once the combination chamber 426 has been removed from the intermediate tube 418 and aerosol holding chamber 412, the end passage cap 446 may be installed over the passages 430 and 434 to close the combination chamber 426.

Figure 10:
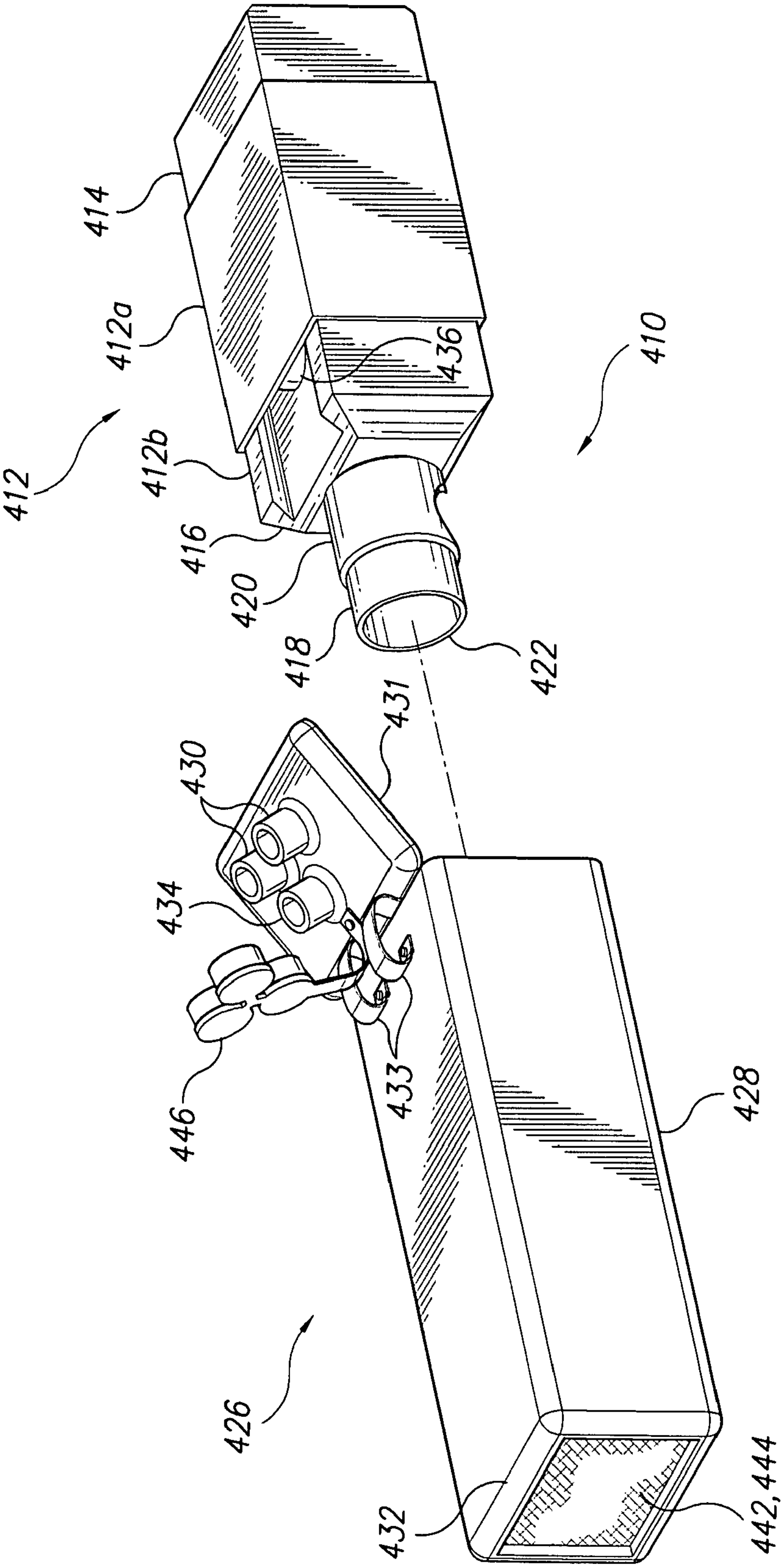
FIG. 10 is an exploded perspective view of the inhaler of FIG. 9, showing the opened end of the recirculation chamber for insertion of the holding chamber therein.
Figure 11:
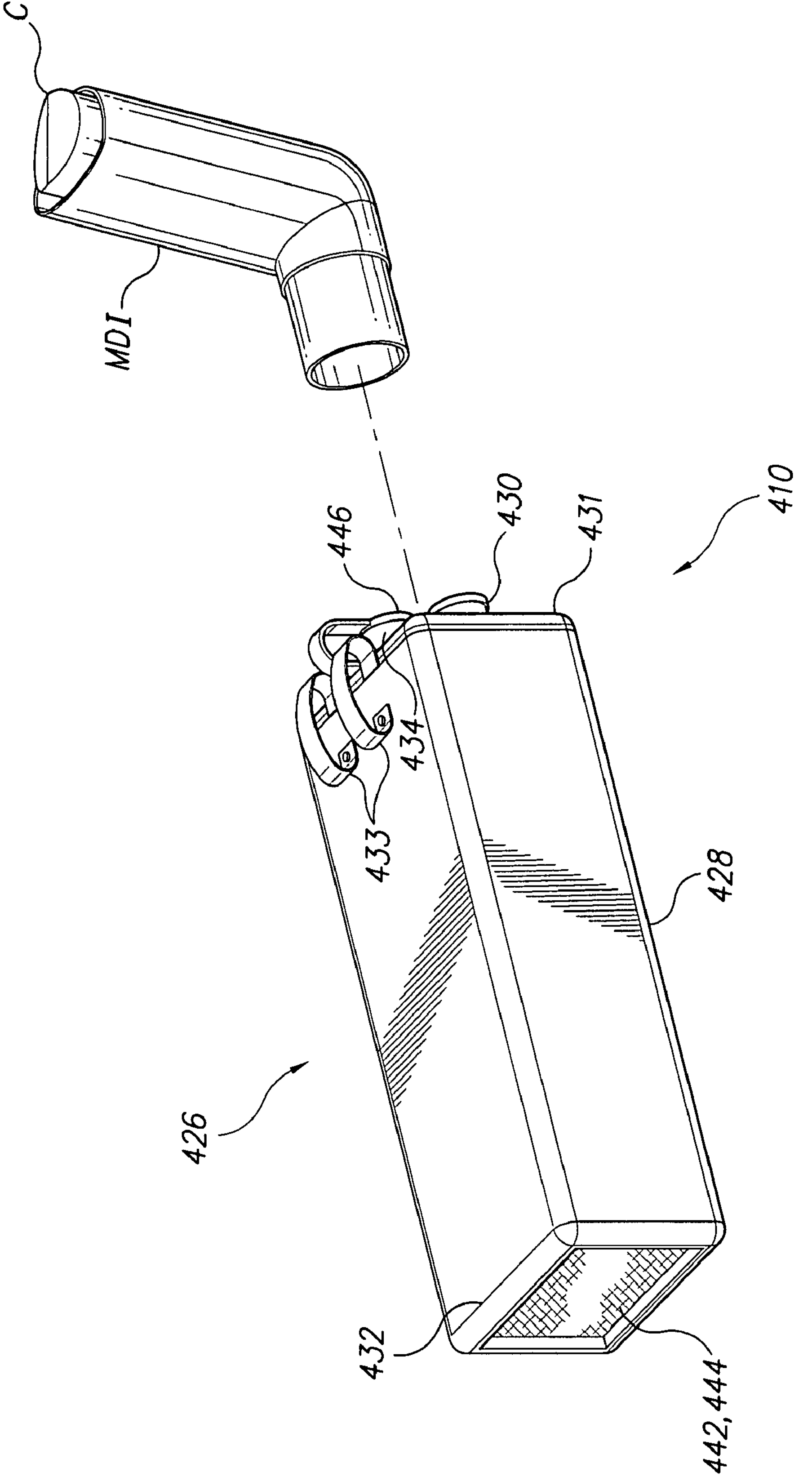
FIG. 11 is an exploded perspective view of the inhaler of FIGS. 9 and 10, showing the closed recirculation chamber and the aerosol medication holder separated therefrom.

At this point, the combination chamber cover 431 is opened (again, in a suitable location due to the release of vapor contained therein), and the collapsed aerosol holding chamber 412 is inserted into the combination chamber for storage therein. The MDI with its canister C or the nebulizer N will have been removed previously from the medication dispenser end 414 of the aerosol holding chamber, as shown in FIG. 10 of the drawings. The combination chamber cover 431 is closed over the end of the combination chamber 426 to complete the storage of the device.

It is to be understood that the present invention is not limited to the embodiments described above, but encompasses any and all embodiments within the scope of the following claims.

I claim:

1. An inhaler for aerosol medication, comprising:

an aerosol holding chamber having a medication dispenser attachment end and a delivery end opposite the medication dispenser attachment end;

an intermediate tube having a first end attached to the delivery end of the aerosol holding chamber, and a user interface device attachment end opposite the first end;

a recirculation chamber having an attachment end communicating with the intermediate tube and having a distal end opposite the attachment end;

a recirculation passage extending from the attachment end of the recirculation chamber, the passage indirectly communicating with the intermediate tube; and a user interface device extending from the user interface device attachment end of the intermediate tube.

2. The inhaler for aerosol medication according to claim 1, wherein the user interface device comprises a mouthpiece, said recirculation passage extending between said recirculation chamber and said aerosol holding chamber.

3. The inhaler for aerosol medication according to claim 1, wherein the user interface device comprises a face mask, the attachment end of the recirculation chamber being attached to the face mask, the recirculation passage extending from the recirculation chamber to the face mask.

4. The inhaler for aerosol medication according to claim 1, wherein the recirculation chamber is selected from the group consisting of recirculation chambers having rigid shells and flexible bag recirculation chambers.

5. The inhaler for aerosol medication according to claim 1, further including an exhalation filter disposed within the distal end of the recirculation chamber.

6. The inhaler for aerosol medication according to claim 5, further including a one-way check valve disposed in the distal end of the recirculation chamber, the one-way check valve permitting outflow through the exhalation filter and blocking inflow through the exhalation filter.

7. The inhaler for aerosol medication according to claim 1, further including a one-way check valve disposed between the aerosol holding chamber and the user interface device, the one-way check valve permitting flow from the aerosol holding chamber into the user interface device and blocking flow from the user interface device to the aerosol holding chamber.

8. The inhaler for aerosol medication according to claim 1, further including a one-way check valve disposed between the recirculation chamber and the aerosol holding chamber, the one-way check valve permitting flow from the recirculation chamber into the aerosol holding chamber and blocking flow from the aerosol holding chamber to the recirculation chamber.

9. An inhaler for aerosol medication, comprising:

a telescoping aerosol holding chamber having an outer portion forming a medication dispenser attachment end, an inner portion forming a delivery end opposite the medication dispenser attachment end, and a selectively closable cover extending from the outer portion;

an intermediate tube having a first end attached to the delivery end of the aerosol holding chamber and a user interface device attachment end opposite the first end;

a collapsible bellows recirculation chamber having an attachment end communicating with the intermediate tube and a distal end opposite the attachment end;

a recirculation passage extending from the attachment end of the recirculation chamber, the passage indirectly communicating with the intermediate tube; and a user interface device extending from the user interface device attachment end of the intermediate tube.

10. The inhaler for aerosol medication according to claim 9, wherein the user interface device is selected from the group consisting of a mouthpiece and a face mask.

11. The inhaler for aerosol medication according to claim 9, further including an exhalation filter disposed within the distal end of the recirculation chamber.

12. The inhaler for aerosol medication according to claim 11, further including a one-way check valve disposed in the distal end of the recirculation chamber, the one-way check valve permitting outflow through the exhalation filter and blocking inflow through the exhalation filter.

13. The inhaler for aerosol medication according to claim 9, further including a one-way check valve disposed between the aerosol holding chamber and the user interface device, the one-way check valve permitting flow from the aerosol holding chamber into the user interface device and blocking flow from the user interface device to the aerosol holding chamber.

14. The inhaler for aerosol medication according to claim 9, further including a one-way check valve disposed between the recirculation chamber and the aerosol holding chamber, the one-way check valve permitting flow from the recirculation chamber into the aerosol holding chamber and blocking flow from the aerosol holding chamber to the recirculation chamber.

15. An inhaler for aerosol medication, comprising:

a telescoping aerosol holding chamber having an outer portion forming a medication dispenser attachment end and an inner portion forming a delivery end opposite the medication dispenser attachment end;

an intermediate tube having a first end attached to the delivery end of the aerosol holding chamber and a user interface device attachment end opposite the first end;

a combination recirculation and aerosol holding chamber storage chamber having a rigid shell forming an attachment end removably connected to the intermediate tube, a distal end opposite the attachment end, and a selectively openable cover disposed upon the attachment end;

a recirculation passage extending from the attachment end cover of the combination recirculation and aerosol holding chamber storage chamber, the passage indirectly communicating with the intermediate tube; and a user interface device extending from the user interface device attachment end of the intermediate tube.

16. The inhaler for aerosol medication according to claim 15, wherein the user interface device is selected from the group consisting of a mouthpiece and a face mask.

17. The inhaler for aerosol medication according to claim 15, further including an exhalation filter disposed within the distal end of the combination recirculation and aerosol holding chamber storage chamber.

18. The inhaler for aerosol medication according to claim 17, further including a one-way check valve disposed in the distal end of the combination recirculation and aerosol holding chamber storage chamber, the one-way check valve permitting outflow through the exhalation filter and blocking inflow through the exhalation filter.

19. The inhaler for aerosol medication according to claim 15, further including a one-way check valve disposed between the aerosol holding chamber and the user interface device, the one-way check valve permitting flow from the aerosol holding chamber into the user interface device and blocking flow from the user interface device to the aerosol holding chamber.

20. The inhaler for aerosol medication according to claim 15, further including a one-way check valve disposed between the combination recirculation and aerosol holding chamber storage chamber and the aerosol holding chamber, the one-way check valve permitting flow from the combination recirculation and aerosol holding chamber storage chamber into the aerosol holding chamber and blocking flow from the aerosol holding chamber to the combination recirculation and aerosol holding chamber storage chamber.

* * * * *